United States Patent [19]
Tolbert et al.

[11] 4,289,854
[45] Sep. 15, 1981

[54] CELL CULTURE METHOD AND APPARATUS

[75] Inventors: William R. Tolbert, Manchester; Mary M. Hitt, St. Louis; Joseph Feder, University City, all of Mo.

[73] Assignee: Monsanto Company, St. Louis, Mo.

[21] Appl. No.: 161,614

[22] Filed: Jun. 20, 1980

[51] Int. Cl.³ .................... C12N 5/02; C12M 3/02
[52] U.S. Cl. .................................. 435/241; 435/286
[58] Field of Search ............... 435/241, 240, 284, 285, 435/286

[56] References Cited

U.S. PATENT DOCUMENTS

| | | | |
|---|---|---|---|
| 820,405 | 5/1906 | Dunlap | |
| 2,958,517 | 11/1960 | Harker et al. | 435/286 |
| 2,991,051 | 4/1961 | Jones | 259/107 |
| 3,039,932 | 6/1962 | McLemans et al. | 435/286 X |
| 3,572,651 | 3/1971 | Harker | 435/316 X |
| 3,622,129 | 11/1971 | Mazowski | 366/247 |
| 3,649,465 | 3/1972 | Scharf et al. | 435/316 X |
| 4,036,693 | 7/1977 | Levine et al. | 435/241 X |
| 4,166,768 | 9/1979 | Tolbert et al. | 435/286 |
| 4,178,209 | 12/1979 | Tolbert et al. | 435/286 X |
| 4,189,534 | 2/1980 | Levine et al. | 435/2 |

OTHER PUBLICATIONS

A. L. van Wezel et al., Process Biochemistry, vol. 28, pp. 6–8, 1978.
Kim J. Mitchell and Wayne Wray, Experimental Cell Research, vol. 123, pp. 452–455; 1979.

Primary Examiner—Robert J. Warden
Attorney, Agent, or Firm—Scott J. Meyer; James W. Williams, Jr.

[57] ABSTRACT

A cell culture system and apparatus is provided for the agitated suspension culturing of mammalian cells in a flask assembly in which the culture medium and cells are gently agitated by the slow rotation of agitator means suspended downwardly in the culture medium and having at least one flexible sheet with a relatively large surface area which is positioned on the agitator in a manner to allow it to billow like a sail as liquid spills from its trailing edge during said rotation of the agitator means.

8 Claims, 9 Drawing Figures

CELL CULTURE METHOD AND APPARATUS

BACKGROUND OF THE INVENTION

This invention relates to a suspension cell culture system and apparatus therefor. More particularly, this invention relates to an agitated suspension cell culture system and agitator apparatus therefor.

In recent years there has been rapid growth in the development of various methods for the culturing of cells in suspension. The attainment of high cell densities is a primary objective of many of these approaches. The use of a cell culture vessel with controlled agitation by means of a magnetic stirrer bar or a mechanically driven impeller on a shaft is a typical feature of these methods. Examples of such apparatus are disclosed in U.S. Pat. Nos. 2,958,517; 3,039,932; 3,572,651; 3,622,122; and 3,649,465. These are essentially batch type spin culture devices or spinner flasks in which the cells are incubated in a fixed amount of nutrient under appropriate culture conditions until cell growth has ceased.

Continuous cell culture systems and apparatus also have been described heretofore in which fresh culture medium can be added and spent medium can be separated from the growing cells by filtration and withdrawn from the flask on a continuous or semicontinuous basis as seen from U.S. Pat. Nos. 4,166,768 and 4,178,209.

While ordinary suspension cultures are suitable for growth of certain mammalian cell lines, other cells, and particularly human diploid cells, require support surface means for cell attachment. Examples of such cell culture systems are the monolayer growth systems in T-flasks, roller bottles, artificial capillary propagators and multi-plate propagators. In order to provide the advantages of large scale suspension culture with provision for cell attachment, microcarrier systems have been developed. The successful use of microcarriers for cell culture was first reported by van Wezel, *Nature* 216, 64-5 (1967). The method of van Wezel consisted of growing cells as monolayers on the surface of positively charged DEAE-Sephadex ® beads suspended in culture media in a stirred vessel. The stirred vessel used by van Wezel was the Bilthoven microbial culture unit described by van Hemert, *Biotech. Bioeng.* VI, 381-401 (1964). Further description of that system is described by van Wezel et al., *Process Biochem.*, March 1978, pp. 6-8 and 28, wherein it is stated that as far as cultivation of very sensitive cell types, such as human diploid cell strains is concerned, the system is still not completely satisfactory.

A modification of the van Wezel method is described by Levine et al., *Somatic Cell Genetics* 3, 149-55 (1977) and U.S. Pat. Nos. 4,036,693 and 4,189,534. This system uses essentially a spinner flask with a magnetically driven stirrer bar.

Although the foregoing suspension cell culture systems have their advantages, they do not provide the desired gentle agitation for certain fragile cell types such as human diploid cells. The present invention provides a suspension cell culture system and apparatus which is directed to overcome that problem and which facilitates a gentle agitation that is useful for sensitive cells as well as fragile microcarriers.

BRIEF DESCRIPTION OF THE INVENTION

In accordance with the present invention, an improved cell culture system and apparatus is provided for the agitated suspension culturing of cells. This system comprises culturing in a flask assembly in which the culture medium is gently agitated by the slow rotation of one or more relatively large surface area, flexible sheets of an agitator means suspended downwardly in the culture medium. The flexible sheets have a total surface area on one side which preferably ranges from about 0.25 to about 1.0 times the available traversable cross-sectional area of the culture fluid-containing portion of the culture vessel. These flexible sheets are positioned on the agitator in a manner to allow them to billow like sails as liquid spills from their trailing edges during rotation of the agitator means, preferably within a range of from about 5 to about 100 rpm.

DETAILED DESCRIPTION OF THE INVENTION

While the specification concludes with claims particularly pointing out and distinctly claiming the subject matter regarded as forming the present invention, it is believed that the invention will be better understood from the following description taken in connection with the accompanying drawings in which:

Figure 1:
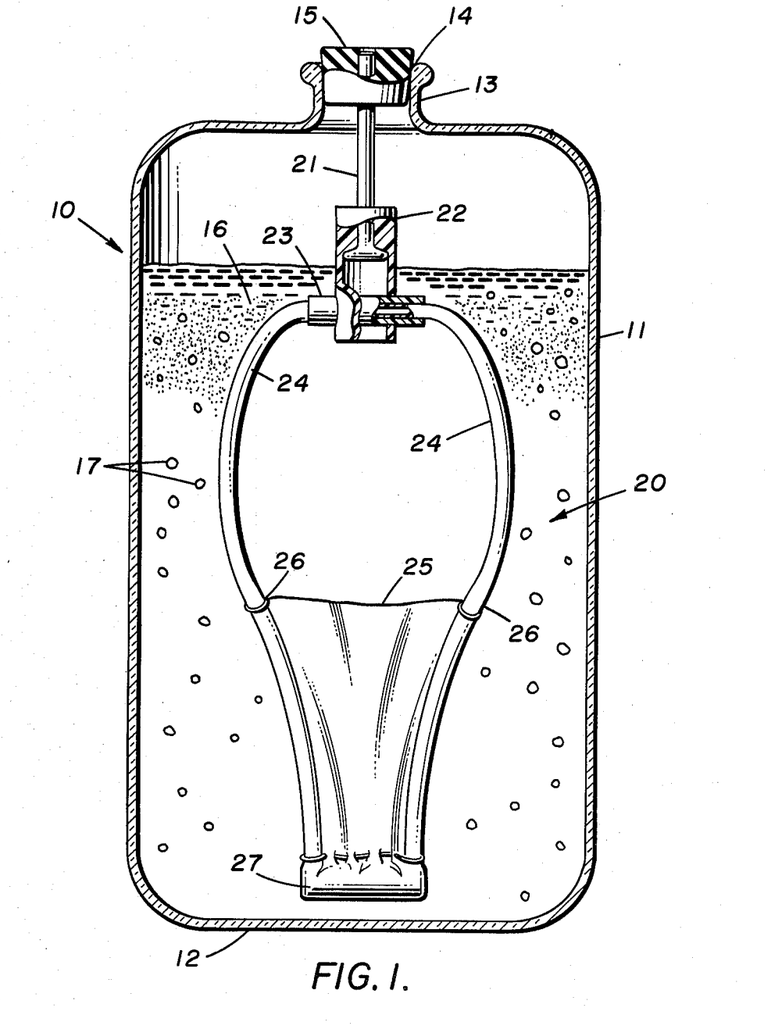
FIG. 1 is a side elevation view partly in cross section showing an embodiment of the cell culture apparatus of the present invention.

Now with particular reference to FIG. 1, reference numeral 10 refers generally to a flask or culture vessel which can be used for the suspension culturing of mammalian and other animal cells. The flask preferably is made of clear glass or non-toxic rigid plastic materials but also can be made of biocompatible metals such as, for example, stainless steel. The flask is shown to have a generally cylindrical form with sidewalls 11, bottom 12, neck portion 13 and mouth 14. It will be appreciated, however, that other configurations of the flask or culture vessel can be employed. In FIG. 1, the mouth is shown to be closed with a removable stopper 15 having a single hole in its center.

Flask 10 is shown to be partially filled with culture fluid 16 in which the cells 17 (exaggerated in size for clarity) are suspended. For cell attachment purposes, microcarriers can also be suspended in the culture fluid.

Positioned vertically in the flask is a rotatable agitator unit 20 which is suspended downwardly from the top by a stationary shaft 21. Shaft 21 is adapted to frictionally fit in the central opening or hole of stopper 15.

The agitator unit 20 is shown to have a rotatable sleeve member 22 journaled for rotation about the stationary shaft 21, a cross piece member 23 fixed in said sleeve member and having a longitudinal axis transverse to the vertical axis of said shaft, a pair of arms 24 downwardly depending from opposite ends of said cross piece member, and a relatively thin, flexible sheet 25 suspended between said arms. The flexible sheet is fastened to the agitator arms, such as by wire means, only at the lower end of each arm and at an upper position, such as, e.g. at about a mid-point 26, along the length of each arm and left unfastened between these attachment points on each arm. A magnetic stirrer bar 27 is also shown to be removably fastened to the lower ends of the agitator arms. The agitator unit can be caused to rotate about shaft 21 by activation of a revolving U-shaped or bar magnet (not shown) positioned under the cell culture flask.

Sheet 25 must have flexibility such as to allow it to yield to the influence of the liquid flow during rotation of the agitator whereby it can billow out like a sail and assume a concave forward facing configuration. The flexible sheet also must remain unattached to the agitator arms for a substantial distance intermediate the upper and lower attachment points to permit such billowing.

The relatively thin, flexible agitator sheet 25 can be made of fine mesh cloth or fabric, plastic film or metal foil, and other such permeable or impermeable flexible sheet materials, for example a nylon screen cloth or a flexible fiberglass sheet. A mono screen nylon cloth available under the trademark NITEX® from Tetko, Inc., of Elmsford, N.Y., having nominal mesh openings of about 110$\mu$ and a thickness of about 0.005 inch (0.0127 cm) is eminently suitable for use in this invention.

During rotation, the agitator unit of FIG. 1 has the appearance of a bowed swing with the stirrer bar representing the swing's seat. The flexible sheet 25 is shown to have an inverted trapezoidal shape in which the upper side of the sheet is preferably longer than the lower side of the sheet to provide additional freedom for the sheet to flex and billow like a sail with the liquid flow during rotation of the agitator unit. The arms of the agitator can be made of a relatively flexible material such as silicone tubing to further facilitate the billowing effect of sheet 25 during such rotation. During operation of the agitator the level of the culture fluid in the culture flask preferably is kept above the flexible sheet but below the bearing means in the sleeve member.

Figure 2:
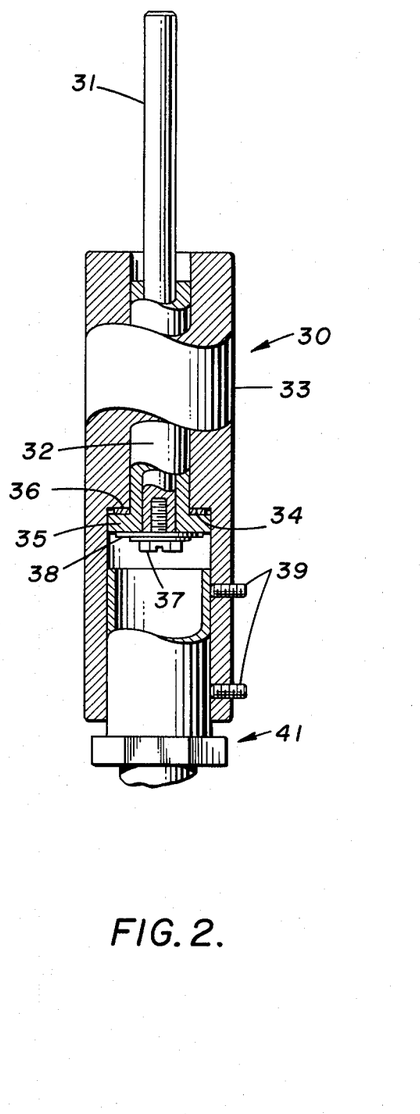
FIG. 2 is a side elevation view partly in cross section showing a sleeve sub-assembly in another embodiment of the invention.
Figures 3, 4:
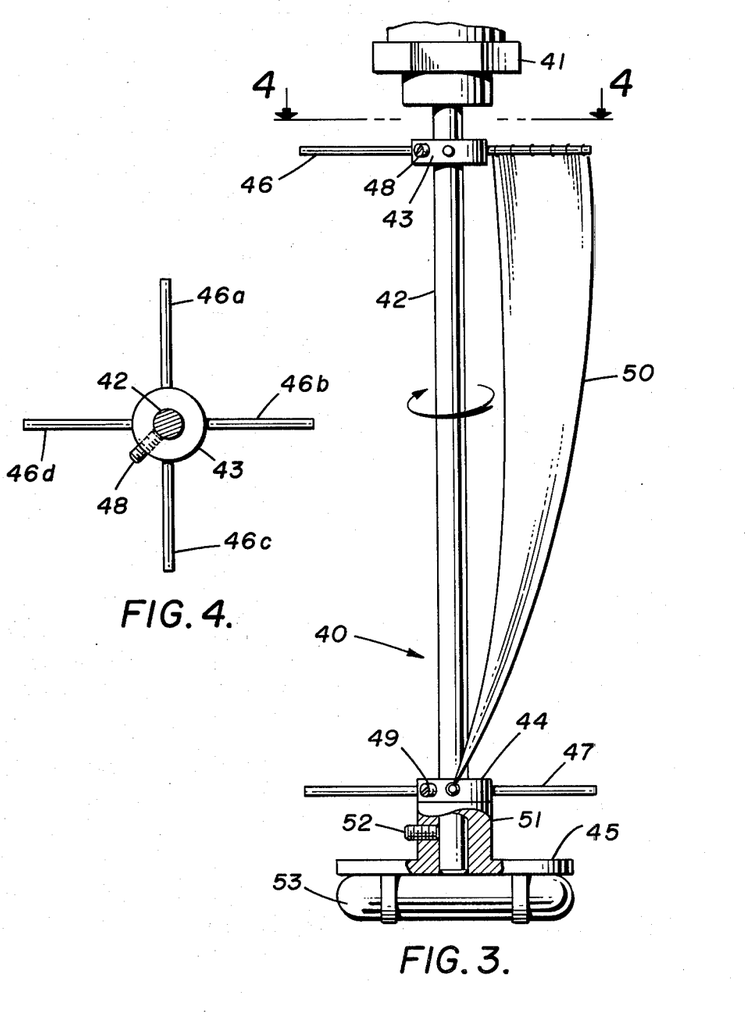
FIG. 3 is a side elevation view partly in cross section showing an agitator unit for use with the sleeve sub-assembly of FIG. 2.
FIG. 4 is a cross section of a ring holder of the agitator unit of FIG. 3 taken along the line 4—4.

In another embodiment of the invention, shown in FIGS. 2 to 4, a series of four flexible sheets is suspended from the agitator unit (only one sheet shown). More particularly, FIG. 2 shows a sleeve sub-assembly 30 which is adapted for suspension from the top of a cell culture flask by a central shaft as in the embodiment of FIG. 1 and which is further adapted to hold suspended downwardly therefrom the agitator unit 40 of FIG. 3 through a connector 41. FIG. 4 shows one of a pair of ring holders adapted for suspending a flexible sheet therebetween on the agitator unit 40. The agitator unit is adapted for suspending four such flexible sheets.

In FIG. 2, the sleeve sub-assembly 30 is suspended downwardly from the top by a stationary shaft 31. As in the embodiment of FIG. 1, the shaft is adapted for frictional engagement in the central opening or hole of a stopper such as stopper 15.

The sleeve sub-assembly 30 is shown to have a stationary inner sleeve member 32 and a rotatable outer sleeve member 33. The inner sleeve member is adapted for frictionally engaging shaft 31 while the outer sleeve member is adapted for low-friction or relatively frictionless engagement of said inner sleeve member. Outer sleeve member 33 has an inverted internal shoulder portion 34 which is shown to rest on an annularly flanged seat portion 35 of the inner sleeve member with an intermediately positioned O-ring bearing 36. The inner sleeve member can be tightened to the shaft 31 by screw 37 and washer 38 as shown in FIG. 2 or by other such conventional fastener means. The outer sleeve member thus rotates with the agitator unit while the inner sleeve member remains stationary with shaft 31. Use of Teflon® plastic or plastic coated steel or glass filled Teflon for the fabrication of the inner sleeve and bearing parts provides suitable bearing surfaces which require no lubrication for low-friction engagement of parts.

In FIG. 3, the agitator unit 40 is shown to be suspended downwardly from the sleeve assembly through a connector 41. For this purpose, commercially available connectors such as, for example, Swagelok® connectors, can be used for convenient, rapid connecting and disconnecting of the union between the sleeve sub-assembly and the agitator unit. This is particularly useful for interchanging of agitator units with the sleeve sub-assembly. Connector 41 can be fixed to the sleeve sub-assembly by set screws 39 as shown in FIG. 2 or by other such conventional fastener means.

The agitator unit 40 of FIG. 3 is shown to have a shaft 42 and, positioned thereon, an upper ring holder 43, a lower ring holder 44 and a disc shaped, bottom plate 45. This agitator unit can be coupled to the sleeve sub-assembly of FIG. 2 by convenient coupling of shaft 42 with connector 41 as shown. Each ring holder of the agitator unit is equipped with a plurality of outwardly extending arms. Thus, as illustrated in FIG. 4, upper ring holder 43 has four arms 46a, 46b, 46c, and 46d, which are substantially equidistantly spaced apart, radiating outwardly from the center of the ring. Each said arm is adapted to hold suspended therefrom a flexible sheet 50. The lower ring holder 44 similarly has four arms 47, corresponding to upper arms 46, which are adapted to hold the lower ends of flexible sheets 50. Each end of sheet 50 can be conveniently looped over the arm of ring holders 43 and 44 and sewn together at the edge of the sheet or otherwise fastened to the arm. Ring holders 43 and 44 can be conveniently tightened onto shaft 42 with set screws 48 and 49, or other such fastening means, and adjusted to any position along the length of shaft 42 or rotated to any position within a 360° orientation around said shaft. Thus, vertical adjustments can be made to accommodate various lengths of flexible agitator sheets. Rotational adjustments can be made in one ring holder relative to the other ring holder to provide scoop-like configurations to the flexible sheets. The lower ring holder 44 is advanced preferably about 45° to about 135°, and most preferably about 90° as illustrated, ahead (in the direction of agitator rotation shown by the arrow around shaft 42) of the upper ring holder 43 as shown in FIG. 3. This scoop-like configuration will help provide a lifting action during the agitation. Conversely, the upper ring holder can be similarly advanced ahead of the lower ring holder to facilitate a downward flow of medium along the surface of the agitator sheet and an upward flow of medium along the walls of the culture vessel. The bottom plate 45 is shown to have an elevated central annular portion 51 to accommodate set screw 52 for fastening to the lower end of shaft 42. One or more magnetic stirrer bars, such as bar 53, is then attached to the bottom plate 45 to facilitate rotation of the agitator unit in a manner similar to the embodiment of FIG. 1. It will be appreciated that the bottom plate can assume various other configurations which will enable it to hold the stirrer bars in a generally horizontal plane during rotation of the agitator.

Figure 5:
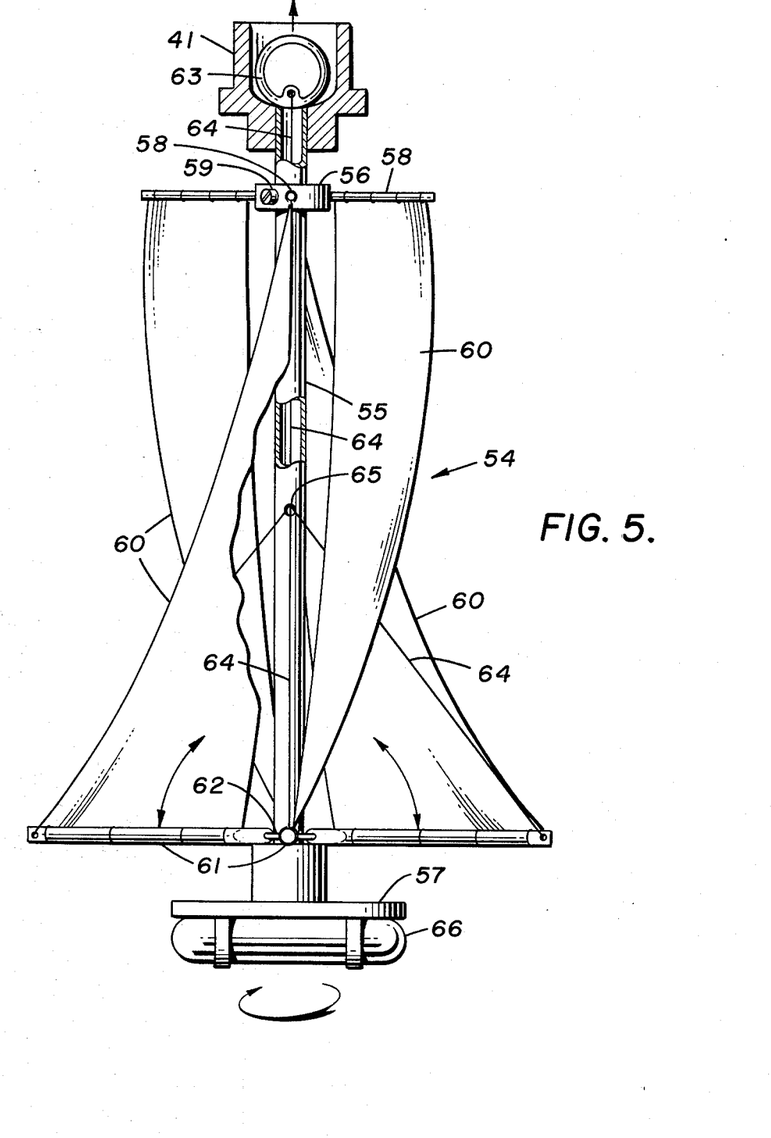
FIG. 5 is a side elevation view partly in cross section showing another embodiment of an agitator unit for use with the sleeve sub-assembly of FIG. 2.

Another embodiment of the agitator unit which can be coupled to a sleeve sub-assembly as in FIG. 2 through a quick-connect coupler or other such means is shown in FIG. 5. Thus, agitator unit 54 is shown to have a hollow shaft 55 and, positioned thereon, an upper ring holder 56 and a bottom plate 57. The upper ring holder is provided with a series of outwardly extending arms 58, as in the embodiment of FIGS. 3 and 4, each of which said arm is adapted to hold suspended therefrom a flexible sheet 60. The ring holder is shown to be removably fastened to the shaft 55 with a set screw 59 for vertical adjustment of the flexible agitator sheet. In this embodiment, sheet 60 is trapezoidal in shape with a substantially wider end at the bottom than at the top. The lower edge of the sheet is held in its outwardly extended position by attachment to bar 61. This trapezoidal shape provides a scoop-like effect in the flexible sheet and a lifting action during rotation of the agitator unit. The scoop-like effect can be further enhanced by positioning the bar 61 ahead (in the direction of agitator rotation shown by the arrow of the bottom of FIG. 5) of the upper ring holder 56 in a manner similar to that shown in the embodiment of FIG. 3.

In order to facilitate insertion and removal of the agitator unit 54 from a cell culture flask having a restricted neck portion as in FIG. 1, the lower, wider end of sheet 60 is attached to a bar 61 which is pivotably linked to shaft 55 such as with pivot bar 62. The agitator unit is further provided with a retaining ring 63 positioned within the bore of connector 40 and a line means such as a wire or string 64 e.g., a nylon suture string. String 64 is knotted to the retaining ring 63 and extends downwardly in the bore of shaft 55, exits through opening 65 of the shaft and leads to the outer extremity of bar 61 where it is again knotted or otherwise fastened to the bar. To insert or remove the agitator unit from the flask, the sleeve sub-assembly can be uncoupled from the agitator unit at connector 41 and the retaining ring can then be pulled upwardly (as shown by the arrow) to thereby pivot bar 61 into a vertical position. String 64 can also extend downwardly from opening 65 to a vertically slidable pivot bar means 62 in another adaptation of this embodiment as illustrated in FIG. 5 for pulling upwardly on bar 61 from the center.

Agitator unit 54 also is provided with at least one magnetic stirrer bar 66 which can be attached to bottom plate 57 to facilitate rotation as in the embodiment of FIG. 1.

Figure 6:
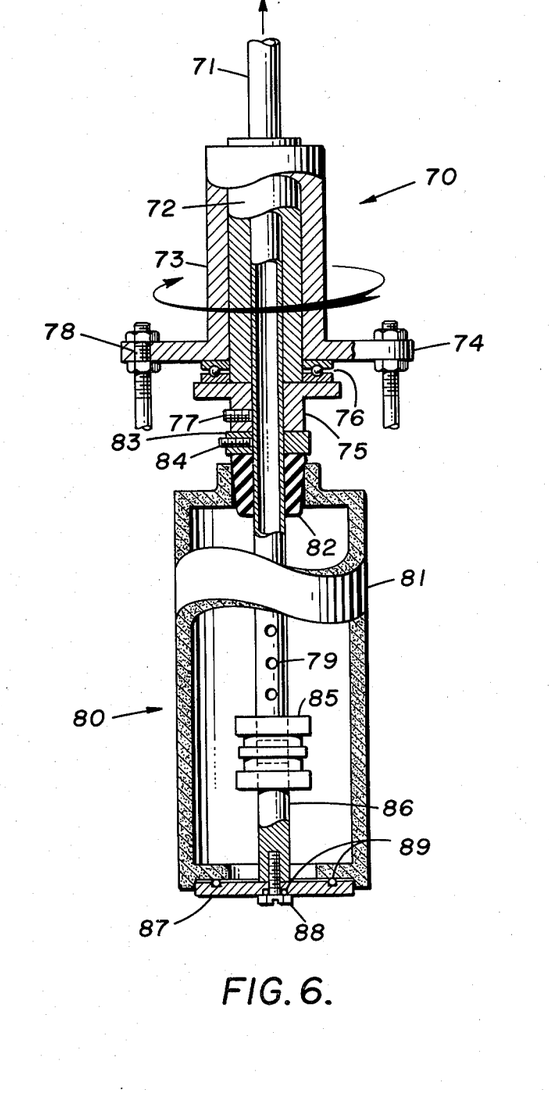
FIG. 6 is a side elevation view partly in cross section showing a sleeve sub-assembly and filter unit in another embodiment of the invention.

In a further embodiment of the invention as illustrated in FIGS. 6 to 9, the agitator unit can be used in cooperation with a filter unit. With particular reference to FIG. 6, reference numeral 70 refers generally to a sleeve sub-assembly and reference numeral 80 refers generally to a stationary filter unit, both of which are positioned on a stationary central shaft 71. As in the embodiment of FIG. 1, the shaft is adapted to frictionally fit in the central opening or hole of stopper 15 at the upper end of the shaft. In this embodiment, shaft 71 is hollow and is provided with at least one opening 79 at the lower end of the shaft which extends into the cavity of filter unit 80.

The sleeve sub-assembly 70 is shown to have a stationary inner sleeve member 72 and a rotatable outer sleeve member 73. The inner sleeve member is adapted for frictional engagement of shaft 71 while the outer sleeve member is adapted for low-friction or relatively frictionless engagement of the inner sleeve member. Outer sleeve member 73 has an outwardly extending annular flange portion 74 at its lower end which is shown to rest on an annularly flanged bearing support ring 75 with an intermediately positioned ball bearing assembly 76. The inner sleeve member can be supported on the shaft 71 with support ring 75 which is fastened to the shaft with set screw 77. The annularly flanged portion of outer sleeve 73 is further adapted to hold the agitator unit 90 by attachment at circumferentially disposed openings 78 as shown in greater detail in FIG. 7.

In FIG. 6, filter unit 80 is shown to have a generally cylindrical body portion 81 with central openings at the top and bottom. An elastomeric stopper 82 with a central opening or hole for frictional placement of the shaft 71 is used to close the top opening of the filter unit while a bottom plate 87 is used to close the lower opening of the filter unit. A filter unit retaining ring 83 is tightened against the top of stopper 82 and fastened to the shaft with set screw 84. The lower end of shaft 71 is seen to be attached to the bottom of the filter unit through a connector 85, rod 86 and disc shaped bottom plate 87. Plate 87 is sealingly fastened to the filter unit with a screw 88 and tightened against O-ring seals 89.

Figures 7, 8, 9:
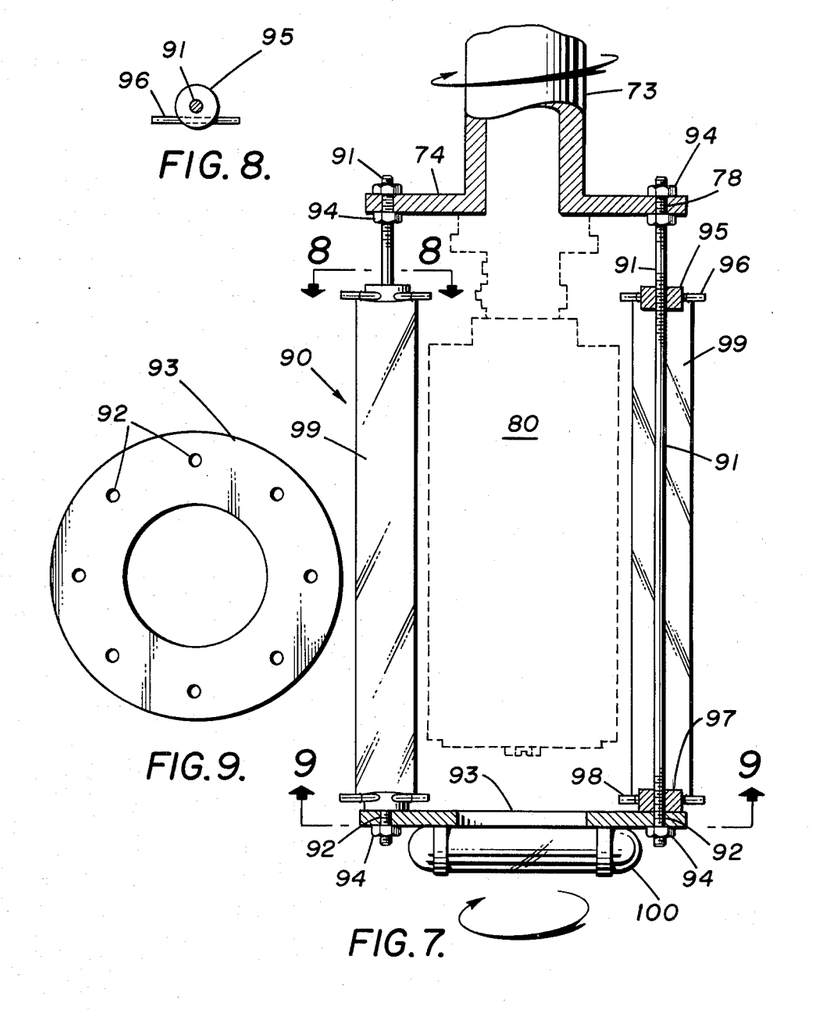
FIG. 7 is a side elevation view partly in cross section showing an agitator unit for use with the sleeve sub-assembly and filter unit of FIG. 6.
FIG. 8 is a cross section of a ring holder of the agitator unit of FIG. 7 taken along the line 8—8.
FIG. 9 is a cross section of the bottom ring plate of the agitator unit of FIG. 7 taken along the line 9—9.

In FIGS. 7 to 9, the rotatable agitator unit 90 is shown to be concentrically disposed about filter unit 80 (shown with dotted lines in FIG. 7 and in greater detail in FIG. 6). The agitator unit is suspended downwardly from the sleeve sub-assembly of FIG. 6 by a series of substantially equidistantly spaced apart, threaded rods 91. These rods are held in their spaced apart relationship by positioning in circumferentially disposed openings 78 of flange portion 74 of the outer sleeve member and similar such openings 92 of an annular plate 93 having the same diameter as flange portion 74 and by fastening with nuts 94. FIG. 9 illustrates provision for eight such rods in the agitator unit.

Each rod 91 in agitator unit 90 is shown to have positioned thereon a threaded upper ring holder 95 having outwardly extending arms 96 and a similar threaded lower ring holder 97 having outwardly extending arms 98 with a flexible sheet 99 suspended between said upper and lower arms. Ring holders 95 and 97 can be raised or lowered to any desired position on rods 91 to accommodate various lengths of sheet 99 and can be rotated within a 360° orientation around said rods to provide various pitches in sheet 99 relative to the vertical axis of the agitator unit.

Agitator unit 90 also is provided with at least one magnetic stirrer bar 100 which can be attached to annular plate 93 to facilitate rotation as in the embodiment of FIG. 1.

In the embodiment of FIGS. 6 to 9, the filter unit body 81 can be made of microporous porcelain, sintered stainless steel, Teflon ® plastic or other such rigid microporous materials. The pore size of the filter should be smaller than the cells to be filtered, or the carrier particles upon which the cells are attached. In certain instances it is desired to filter all the cells. A pore size of from about 0.2μ to about 5.0μ is suitable for most single cells. In the case of cell aggregates or cells attached to microcarriers, the pore size can be larger but still smaller than the particles to be filtered, e.g., a pore size of from about 25μ to about 75μ in the case of particles of about 100μ in diameter or larger.

The filter unit preferably is suspended to a depth in the cell culture flask such that it lies substantially completely in the fluid medium. A vaccum drawn on the central hollow shaft 71 by a peristaltic pump (not shown) will cause withdrawal of the fluid medium from the flask after passage through the walls of the filter unit and into the filter cavity and thence into the shaft through openings 79. Culture fluid can thus be separated from the residual cells on a continuous or semi-continuous basis.

The cell culture apparatus of this invention can be used with conventional cell culture auxiliary apparatus such as pumping means for pumping in fresh medium from a supply reservoir and pumping out spent medium into an effluent collection reservoir. The flask can be provided with additional openings for such distribution of culture medium, for gas inlet and outlet means, sampling tubes and probes for maintaining pH, liquid level and dissolved oxygen levels.

The cell culture apparatus of this invention also can be operated as a satellite flask in a series with other cell culture reactors and vessels by suitable tubing and pumping means. For example, the apparatus of FIGS. 6 to 9 can serve as a satellite filtering means for a main cell culture flask used in the growth of the cells.

The suspension cell culture apparatus of this invention has been used for the growth of various cells both with and without the presence of microcarriers in the culture medium. Microcarriers have been used for the growth of human diploid cells while mammalian tumor cells have been grown without the presence of the microcarriers. Good results have been obtained when operating over extended periods of time at agitator rotation speeds ranging from about 5 to about 100 rpm and with the surface area of the flexible sheets ranging from about 0.25 to about 1.0 times the available traversable cross-sectional area of the culture vessel and with from one to eight such flexible sheets on the agitator.

The cell culture system and apparatus of this invention is adaptable for use with all types of animal cells including, for example, mammalian, fowl, and amphibian cells, as well as plant cells, e.g. carrot cells. Primary cells taken from embryonic, adult or tumor tissues as well as continuous cell lines can thus be used. Examples of typical such cells are primary rhesus monkey kidney cells, baby hamster kidney cells, pig kidney cells, embryonic rabbit kidney cells, mouse embryo fibroblasts, normal human lung embryo fibroblasts, HeLa cells, primary and secondary chick fibroblasts, and various cells transformed with SV-40 or polyoma virus. Specific cell lines which have shown good growth with less debris than obtained with conventional spinner agitators are, for example SK-HEP-1, KNIH, SV-W126, Walker 256, TE-671, RAG, Raji and TCMK-1 cell lines. These are all well known cell lines which are available to the public for research and other purposes from various depositories.

The cell culture system and apparatus of this invention also is adaptable to use with any of the well known tissue culture media such as, for example, Basal Medium Eagle's (BME), Eagle's Minimum Essential Medium (MEM), Dulbecco's Modified Eagle Medium, Medium 199 and the like. These are commercially available tissue culture media and are described in detail by H. J. Morton, *In Vitro* 6, 89–108 (1970). These conventional culture media contain known essential amino acids, mineral salts, vitamins and carbohydrates. They are also frequently fortified with mammalian sera such as fetal bovine serum.

Various other examples will be apparent to the person skilled in the art after reading the disclosure herein without departing from the spirit and scope of the invention. It is intended that all such further examples be included within the scope of the appended claims.

What is claimed is:

1. Apparatus for the suspension culturing of cells comprising
   (A) a hollow flask having an opening at the top,
   (B) shaft means within said flask and supported downwardly from said top opening, and
   (C) a rotatable agitator means supported downwardly from said shaft means, said agitator means having supported thereon at least one flexible sheet, said flexible sheet being thus supported at upper and lower positions of the sheet to permit billowing of said sheet during rotation of the agitator means.

2. Apparatus of claim 1 in which the flexible sheet has a surface area on one side which ranges from about 0.25 to about 1.0 times the available traversable cross-sectional area of the culture fluid-containing portion of said flask.

3. Apparatus of claim 1 in which the agitator means comprises a rotatable shaft and a plurality of flexible sheets, each said sheet being substantially equidistantly spaced apart from each other sheet circumferentially about the vertical axis of said rotatable shaft.

4. Apparatus of claim 3 in which each flexible sheet is supported at said lower position of the agitator means ahead of said upper position relative to the direction of rotation whereby said flexible sheet is provided with a scoop-like configuration.

5. Apparatus of claim 3 in which each flexible sheet is supported at said upper position of the agitator means ahead of said lower position relative to the direction of rotation whereby said flexible sheet is provided with a concave configuration.

6. Apparatus of claim 3 in which said shaft has a hollow bore and a side opening through an outer wall, and in which said flexible sheets are pivotably supported at their lower ends on said shaft with pivot means in combination with line means downwardly disposed from the top of said shaft through said bore and said side opening and secured to said pivot means.

7. Apparatus of claim 1 in combination with a stationary filter unit supported downwardly from said shaft means in which said shaft means has a hollow interior in fluid communication with said top opening of said flask, in which said filter unit has a fluid collection cavity in direct fluid communication with the interior of said shaft means and the top of said flask and a porous peripheral surface having a pore size smaller than the cells to be cultured or the carrier particles on which said cells are attached but sufficiently large to permit permeation of fluid into said fluid collection cavity, and in which said rotatable agitator means is concentrically disposed about said filter unit.

8. In the method of culturing animal cells in agitated liquid suspension of nutrient culture medium, the improvement comprising carrying out the agitation with the apparatus of claim 1.

* * * * *